United States Patent [19]

Buck et al.

[11] 4,247,719

[45] Jan. 27, 1981

[54] PROCESS FOR OBTAINING 2,5-XYLENOL FROM A 2,4-/2,5-XYLENOL MIXTURE

[75] Inventors: William R. Buck; John R. Dodd, both of Ponca City, Okla.

[73] Assignee: Conoco, Inc., Ponca City, Okla.

[21] Appl. No.: 55,087

[22] Filed: Jul. 5, 1979

[51] Int. Cl.³ .................... C07C 37/68; C07C 37/14
[52] U.S. Cl. .................... 568/750; 568/788
[58] Field of Search ............. 568/750, 751, 752, 788

[56] References Cited

U.S. PATENT DOCUMENTS

| | | | |
|---|---|---|---|
| 2,435,087 | 1/1948 | Luten et al. | 568/750 |
| 2,497,971 | 2/1950 | Basterfield | 568/750 |
| 2,586,070 | 2/1952 | Luten et al. | 568/750 |
| 2,802,884 | 8/1957 | D'Alelio | 568/788 |
| 2,917,487 | 12/1959 | Jones et al. | 568/750 |

FOREIGN PATENT DOCUMENTS

| | | | |
|---|---|---|---|
| 1153027 | 8/1963 | Fed. Rep. of Germany | 568/750 |
| 582057 | 11/1946 | United Kingdom | 568/750 |
| 706107 | 3/1954 | United Kingdom | 568/750 |
| 969415 | 9/1964 | United Kingdom | 568/750 |

OTHER PUBLICATIONS

Stevens, "Industrial & Eng. Chem.," vol. 35, No. 6, pp. 655-660.

Primary Examiner—Werren B. Lone
Attorney, Agent, or Firm—Cortlan R. Schupbach, Jr.

[57] ABSTRACT

The relative amount of 2,5-xylenol in a 2,4-/2,5-xylenol mixture is significantly increased by passage of the xylenol mixture together with a suitable tertiary-alkylating agent through a reactor packed with a polymer-bound sulfonic acid catalyst at temperatures of 65°-95° C. and, preferably, 80°-90° C. The product stream from such a reactor under these conditions based on a 50:50 mixture of the two isomers contains a much greater amount of 6-t-alkyl-2,4-xylenol (t-alkylated 2,4-xylenol) than 4-t-alkyl-2,5-xylenol (t-alkylated 2,5-xylenol); consequently the resulting unalkylated 2,4-/2,5-xylenol mixture is greatly enriched in 2,5-xylenol. Recovery of the unalkylated mixture by fractionation thus affords a crude 2,5-xylenol which can be further purified to give pure 2,5-xylenol.

8 Claims, No Drawings

PROCESS FOR OBTAINING 2,5-XYLENOL FROM A 2,4-/2,5-XYLENOL MIXTURE

This invention relates to a method for increasing the relative amount of 2,5-xylenol in mixtures of 2,5-xylenol and 2,4-xylenol. More specifically, this invention relates to such isomer enrichment under critical temperature conditions.

For many applications it is desirable to separate admixtures of 2,4-xylenol and 2,5-xylenol into individual isomers such that each is available in high purity. These materials cannot be separated by fractional distillation since these isomers boil within 0.1° C. of one another. Consequently, other methods of achieving this separation must be utilized. The instant invention provides a method for increasing the amount of 2,5-xylenol in mixtures of 2,4-xylenol and 2,5-xylenol. The invention also provides a method for the production of pure 2,4-xylenol.

The prior art contains many references which relate to phenolic alkylations and dealkylations. Representative but not-exhaustive of such art is U.S. Pat. No. 2,802,884 which describes the use of a sulfonic acid catalyst on a resin matrix as an alkylation/dealkylation catalyst with temperatures greater than or equal to 100° C.

British Pat. No. 582,057 describes a method for separating 2,4-xylenol and 2,5-xylenol, the method comprising butylation of a 2,4-xylenol/2,5-xylenol mixture and then treatment of the butylated mixture with an aqueous alkali solution to remove insoluble 6-t-butyl-2,4-xylenol from the basic solution. The basic solution is then acidified and the recovered 4-t-butyl-2,5-xylenol is then debutylated to afford pure 2,5-xylenol upon fractionation. British Pat. No. 706,107 teaches a related method that shows the use of a sulfuric acid catalyst to alkylate with diisobutylene wherein only 2,4-xylenol is alkylated. U.S. Pat. No. 2,917,487 shows the separation of such mixtures by selective resinification. German Pat. No. 1,153,027 shows that these xylenols can be separated by butylation with isobutylene catalyzed by perchloric acid, followed by separation of the butylated isomers by fractional distillation, and then debutylation of the individual butylated xylenols.

In the prior art, most reactions occur in the temperature range of up to 30° C. U.S. Pat. No. 2,802,884 shows alkylation reactions at temperatures greater than 100° C.

Many of the above processes use aqueous streams in various processing steps. Xylenols are partially soluble in aqueous streams and thus the streams are thereafter contaminated with phenolic compounds. This leads to the loss of phenolic material and presents disposal problems which can become severe.

It is therefore an object of the instant invention to provide a process for substantially increasing the amount of 2,5-xylenol starting from 2,4-xylenol/2,5-xylenol mixtures without using any aqueous treatment. Other objects will become apparent to those skilled in this art as the description proceeds.

It has now been discovered according to the instant invention that 2,5-xylenol can be largely separated from admixture with 2,4-xylenol by passing the 2,5-xylenol/2,4-xylenol mixture together with a suitable tertiary-alkylating agent through a reactor containing a sulfonic acid catalyst on a polymer matrix at a preferred temperature of from 80° to 90° C. The 2,4-xylenol in the product stream is alkylated to a much higher degree than is the 2,5-xylenol isomer, which results in a much higher relative amount of 2,5-xylenol in the unalkylated 2,4-/2,5-xylenol portion of the product stream.

Catalysts useful in the process of the instant invention are any polymer-supported sulfonic acid catalysts which are unreactive under the reaction conditions. Representative examples of such polymers are various sulfonated styrene-divinylbenzene copolymers. Preferred sulfonated divinylbenzene-styrene copolymers are those having at least 2% crosslinking.

Suitable alkylating agents for the purposes of the instant invention are olefins which afford tertiary-alkyl groups upon alkylation. Representative examples of such olefins are 2-methyl-1-butene, 2-methyl-1-pentene, 2-methyl-1-heptene, and isobutylene (2-methyl-1-propene). Of these, isobutylene is the most preferred.

The instant invention is believed to depend upon alkylation occurring under the reaction conditions and simultaneous dealkylation occurring in a highly selective manner, although this is a hypothesis only and has not been proven. Tertiary alkyl groups are necessary in the alkylated product in order for the dealkylation to occur readily under the reaction conditions.

Suitable mole ratios of olefin to xylenol for the purposes of the instant invention are generally from about 0.7 to about 3.0, respectively. However, mole ratios of 1.2 to 1.5, respectively, are preferred. The instant invention can be carried out at a pressure of approximately from 0 to 100 pounds per square inch gauge (psig) although a pressure from 0 to 10 psig is preferred. The instant invention works best at a reactor temperature of from 80° to 90° C. Temperatures near the midpoint of this range are most preferred.

The reaction is highly suitable for a continuous process. When carried out continuously, a liquid hourly space velocity (LHSV) of from 0.4 to 2.5 can be used. However, a LHSV of from 0.5 to 0.8 is preferred.

Once the 2,4-/2,5-xylenol mixture has been passed in the presence of the alkylating agent through the reactor, the product stream from the reactor is fractionated to separate the xylenol portion from the balance of the mixture. Under optimal conditions, the 2,5-xylenol purity after 1 pass (50/50 starting mixture of the two isomers) is approximately 82%. The xylenol portion of the product stream containing mainly 2,5-xylenol can optionally be passed through the reactor one or more additional times in the presence of additional olefin to further raise the 2,5-xylenol purity.

However, as a second alternative, the 2,5-xylenol of approximately 82% purity obtained after 1 pass through the reactor can be further purified by other methods well known to those skilled in the art. Among such methods are fractional crystallization. Still another alternative is to use a combination of these methods in which multiple reactor passes followed by recrystallization are utilized to obtain pure 2,5-xylenol.

The invention is more concretely described with reference to the examples below wherein all parts and percentages are by weight unless otherwise specified. The examples are provided to illustrate the instant invention and not to limit it.

In the examples below, experiments employing the instant invention were conducted using isobutylene and a cresylic acid mixture. The composition of the cresylic acid mixture used in the feed was as set forth below for all examples.

| | |
|---|---|
| 2,3-xylenol | 19.05% |
| 2,4/2,5-xylenol mixtures | 34.69% (48.75% 2,5-xylenol and 51.25% 2,4-xylenol) |
| 2,6-xylenol | 9.88% |
| 2,4,6-trimethylphenol | 29.31% |
| 2,3,6-trimethylphenol | 3.53% |
| pentamethylbenzene | 2.89% |
| phenol and cresols | less than .5% |

EXAMPLES 1 THROUGH 6

A feed consisting of 425 grams of the cresylic acid mixture together with 115 grams of isobutylene was passed through a stainless steel continuous tubular reactor (57 centimeters × 1.30 centimeters inside diameter) packed with 44 grams of polymer-bound sulfonic acid catalyst (Amberlyst 15 ®, Trademark of and sold by Rohm and Haas Company) under the conditions set forth in Table 1.

The product stream was collected in fractions of approximately 20 milliliters (ml). The fractions were analyzed by gas chromatography (GC). The reactor was operated under a given set of conditions at least as long as required for two successive fractions to show no difference in their GC traces. These fractions were then taken as representative of the particular conditions used. The components in the product stream were identified using authentic samples, gas chromatographic analysis, and spectrographic analysis such as nuclear magnetic resonance (nmr) and CG/MS (gas chromatography/mass spectrometry). The selectivity data reported in Table 1 was calculated from gas chromatographic analysis of the product stream.

In Table 1, M represents the moles of isobutylene divided by the moles of all xylenols in the feed. The term "Conv (IB)" is the percent conversion of isobutylene; Conv (2,4-2,5) is the percent conversion of 2,4 and 2,5-xylenol; Conv(26) is the percent conversion of 2,6-xylenol; and Conv(23) is the percent conversion of 2,3-xylenol. The term "Sel(Olig)" is the selectivity for oligomerization of isobutylene. The term "Sel(Butyl)" is the selectivity for butylation with isobutylene. The calculated purity is the 2,5-xylenol purity in the 2,4-/2,5-xylenol mixture calculated using the conversion of 2,4-xylenol and 2,5-xylenol and the ratio of butylated 2,4-xylenol products to butylated 2,5-xylenol products. The measured purity is the purity of 2,5-xylenol in the unreacted 2,4-xylenol/2,5-xylenol mixture. This was determined by gas chromatographic analysis of a silylated mixture. The measured purities in these cases are generally lower than the corresponding calculated purities, apparently due primarily to the fact that the gc peak attributable to 6-t-butyl 2,4-xylenol is enhanced by a coeluted butylated trimethylphenol. The measured purities are the ones determined to be accurate for the purposes of the instant invention. The calculated purities are useful as an approximate guide to purity. The 2,5-xylenol purity is the percentage of 2,5-xylenol in the total 2,4/2,5-xylenol mixture which was not alkylated.

EXAMPLES 7 AND 8

The experiment was repeated in the manner described for Examples 1 through 5 using as feed 423.6 grams of the starting cresylic acid mixture together with 143.2 grams of isobutylene.

EXAMPLES 14 THROUGH 19

The experiment was repeated in the manner described for Examples 1 through 5 using 700 grams of the starting cresylic acid mixture and 307 grams of isobutylene.

Table 1

UPGRADING THE 2,5-XYLENOL PURITY IN A CRESYLIC ACID MIXTURE CONTAINING 2,4-/2,5-XYLENOLS BY SELECTIVE BUTYLATION OVER AMBERLYST-15 ®

| Example | T (°C.) | P (psig) | LHSV (Hr$^{-1}$) | M | Conv (IB) | Conv (24/25) | Conv (26) | Conv (23) | Sel (Olig) | Sel (Butyl) | 2,5-Purity (Calc) | 2,5-Purity (Meas) |
|---|---|---|---|---|---|---|---|---|---|---|---|---|
| 1 | 111 | 3 | .41 | 0.93 | 97.7 | 23 | 100 | 62 | 30 | 70 | 62 | 59 |
| 2 | 71 | 3 | .89 | 0.93 | 99.7 | 46 | 91 | 92 | 25 | 75 | 82 | 73 |
| 3 | 50 | 3 | .71 | 0.93 | 99.5 | 53 | 70 | 80 | 20 | 80 | 45 | 52 |
| 4 | 90 | 3 | .68 | 0.93 | 99.6 | 37 | 99 | 53 | 30 | 70 | 74 | 70 |
| 5 | 61 | 3 | .71 | 0.93 | 99.9 | 44 | 94 | 75 | 22 | 78 | 74 | |
| 6 | 75 | 3 | .92 | 0.93 | 99.8 | 42 | 96 | 64 | 22 | 78 | 80 | |
| 7 | 90 | 3 | 1.10 | 1.16 | 99.4 | 43 | 98 | 63 | 45 | 55 | 77 | |
| 8 | 37 | 3 | 1.06 | 1.16 | 96.5 | 57 | 62 | 82 | 26 | 74 | 32 | |
| 9 | 65 | 3 | .96 | 0.99 | 99.8 | 54 | 93 | 81 | 25 | 75 | 79 | |
| 10 | 71 | 3 | .81 | 0.99 | 99.8 | 48 | 93 | 74 | 30 | 70 | 80 | |
| 11 | 70 | 3 | .40 | 0.99 | 99.8 | 48 | 98 | 72 | 29 | 71 | 86 | |
| 12 | 75 | 3 | .97 | 0.99 | 99.8 | 47 | 91 | 76 | 30 | 70 | 78 | |
| 13 | 81 | 3 | .91 | 0.99 | 99.7 | 47 | 93 | 72 | 32 | 68 | 85 | |
| 14 | 70 | 3 | .81 | 1.50 | 99.5 | 70 | 96 | 87 | 44 | 56 | 69 | |
| 15 | 80 | 3 | .78 | 1.50 | 99.7 | 57 | 98 | 80 | 49 | 51 | 88 | |
| 16 | 90 | 3 | .80 | 1.50 | 99.6 | 50 | 100 | 71 | 50 | 50 | 89 | 80 |
| 17 | 85 | 3 | .80 | 1.50 | 99.6 | 57 | 100 | 77 | 48 | 52 | 94 | 82 |
| 18 | 85 | 50 | .81 | 1.50 | 99.8 | 51 | 100 | 71 | 47 | 53 | 91 | 80 |
| 19 | 85 | 3 | .59 | 1.50 | 99.7 | 57 | 100 | 75 | 47 | 53 | 94 | |

Table 1 shows the 2,5-xylenol content in the 2,4-/2,5-xylenol mixture passing through the reactor is greatly dependent upon the reactor temperature. The greatest amount of 2,5-xylenol in the exiting 2,4-/2,5-xylenol mixture was achieved at temperatures of 80°–90° C. Higher and lower temperatures resulted in considerably lower 2,5-xylenol content. Advantages are seen in the general temperature range of 65° C. to 95° C., but maximum 2,5-xylenol is obtained in the 80° C. to 90° C. range.

The instant invention is based upon the formation of a much greater amount of 6-t-alkyl-2,4-xylenol (t-alkylated 2,4-xylenol) than 4-t-alkyl-2,5-xylenol (t-alkylated 2,5-xylenol) under the conditions of the instant invention. The reasons for this advantage are not known. However, 2,5-xylenol enrichment appears to be due primarily to the extensive dealkylation of 4-t-alkyl-2,5-xylenol and little or no dealkylation of 6-t-alkyl-2,4-xylenol under the conditions of the instant invention. This highly selective dealkylation over a polymer-bound sulfonic acid catalyst is not known in the prior art and is surprising. Both 2,4-xylenol and 2,5-xylenol are readily alkylated under the conditions of the instant invention; consequently, if the above selective dealkylation were not occurring, little or no isomer enrichment would be observed. The instant invention consists of the transformation of a 2,4-/2,5-xylenol mixture into a product mixture containing predominantly 2,5-xylenol and t-alkylated-2,4-xylenol together with olefinic oligomers. Fractionation of the product mixture provides a xylenol fraction that contains a 2,5-xylenol content of up to 82% after one pass through the reactor. Multiple reactor passes can give further enrichment in the 2,5-xylenol purity.

Optionally, 2,4-xylenol can also be obtained in high purity. First, the t-alkylated xylenol portion containing mainly 6-t-alkyl-2,4-xylenol, is fractionated to remove any 4-t-alkyl-2,5-xylenol. The purified 6-t-alkyl 2,4-xylenol (t-alkylated 2,4-xylenol) is then dealkylated under appropriate conditions and fractionated to yield pure 2,4-xylenol. 6-t-alkyl-2,4-xylenols are easily dealkylated over silica-alumina catalysts at temperatures of from about 200°-220° C. and at pressures near atmospheric in fixed-bed reactions.

Debutylation of 6-t-butyl-2,4-xylenol (24M6B) over silica-alumina (Grace 979) in a continuous tubular reactor at 220° C. and LHSV=1.6 in the presence of 0.5 w/% of added water (as steam) was tested in Example 20 to show production of 2,4-xylenol.

EXAMPLE 20

A stainless steel tubular reactor (19"×0.512"(i.d.)) equipped with a thermowell (3.2 millimeter diameter) was used in this experiment. A catalyst bed consisting of 14.65 g of Grace 979 silica-alumina (⅛" extrudate cut further to give pieces ~3/16" long) was packed in the center of the reactor. The catalyst bed was 12" in length and the catalyst bed volume was 38.0 milliliters. Glass beads (sections of ~3.5" length) were used as filler at both ends of the reactor. The reactor was wrapped with nichrome wire over the entire length as the heating element and was then insulated with glass tape. A feed buret, metering pump, and preheater were set up along with the reactor. The reactor was equipped with a water condenser at the product stream outlet which in turn was connected to a wet test meter. The reactor was equipped also with a steam inlet and water preheater (operated at ~200° C.).

In this experiment, the reactor was operated continuously at 220° C. and LHSV=1.6 in the liquid-full mode with feed entering at the bottom of the tubular reactor (positioned vertically). A mixed cresylic feed containing 96.16% 6-t-butyl-2,4-xylenol was used for this experiment. The feed was preheated to 210°-220° C. before entering the reactor. Water was fed into the water preheater (and then into the reactor as steam) at the rate of 0.005 milliliters per minute using a syringe pump as the mixed cresylic feed having more than 95% 6-t-butyl-2,4-xylenol was pumped into the reactor at ~1.00 ml/min.

The liquid product stream was collected in cuts of approximately 22 g (usually cut every 0.5 hour). These samples were analyzed by gas chromatography. The volume of noncondensable gas (isobutylene) was measured with time using a wet test meter. The experiment yielded 2,4-xylenol in selectivities exceeding 97% while converting over 99% of 6-t-butyl-2,4-xylenol.

Process 1 illustrates the essential features of the instant invention.

PROCESS 1

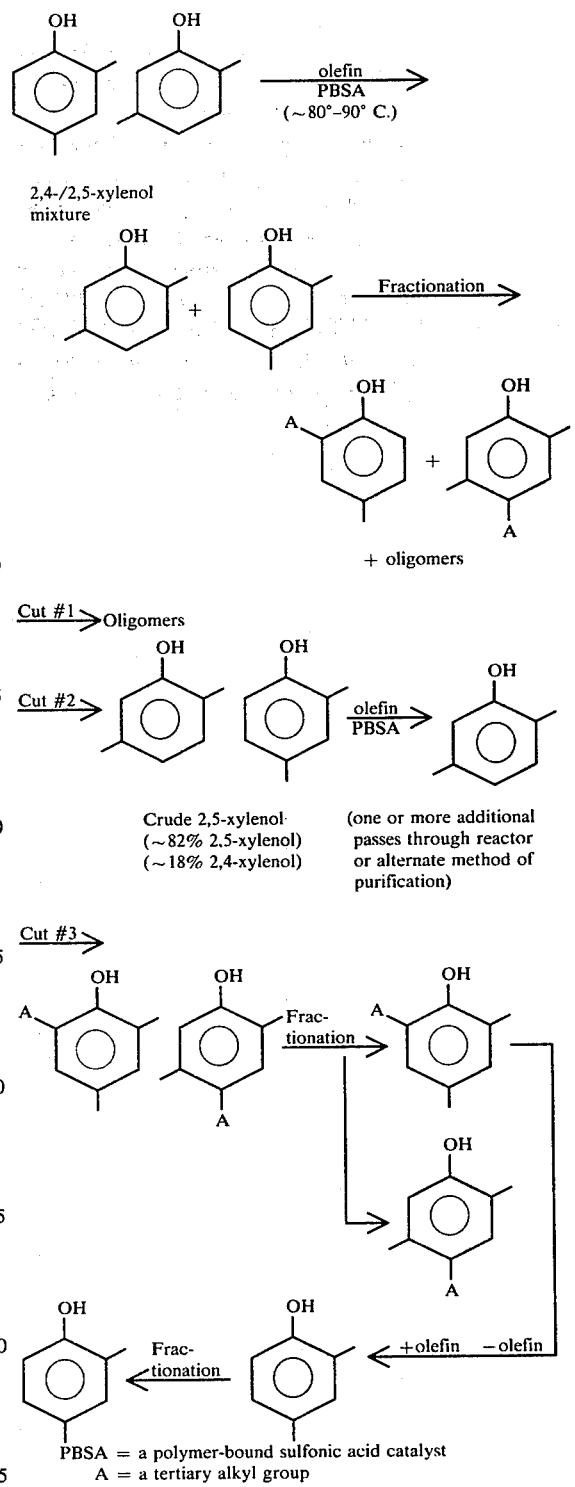

PBSA = a polymer-bound sulfonic acid catalyst
A = a tertiary alkyl group

While certain embodiments and details have been shown for the purpose of illustrating this invention, it will be apparent to those skilled in this art that various changes and modifications may be made herein without departing from the spirit or scope of the invention.

We claim:

1. A method for increasing the content of 2,5-xylenol in a 2,4-/2,5-xylenol mixture which comprises continuously passing the 2,4-xylenol/2,5-xylenol mixture over a polymer supported sulfonic acid catalyst in the presence of an olefin providing tertiary alkylation and selected from the group consisting of 2-methyl-1-butene, 2-methyl-1-pentene, 2-methyl-1-heptene, and 2-methyl-1-propene at a liquid hourly space velocity of from about 0.4 to about 2.5 and recovering a product mixture containing t-alkyl-2,4-xylenol; and t-alkyl-2,5-xylenol together with non-alkylated, 2,4-xylenol and 2,5-xylenol, then fractionating the product mixture to remove tertiary alkylated phenols and recover a 2,4-xylenol/2,5-xylenol mixture having an increased 2,5-xylenol content, the improvement comprising carrying out the reaction at a temperature of from about 60° C. to about 95° C.

2. A method as described in claim 1 wherein the process is carried out at a temperature of from about 80° C. to about 90° C.

3. A method as described in claim 2 wherein the olefin is selected from the group consisting of isobutylene 2-methyl-1-butene, 2-methyl-1-pentene, and 2-methyl-1-heptene.

4. A method as described in claim 3 wherein the olefin is isobutylene.

5. A method as described in claim 4 wherein the catalyst is a sulfonated divinylbenzene-styrene copolymer containing at least 2% crosslinking.

6. A method as described in claim 3 wherein the fractionated product mixture with increased 2,5-xylenol content is repeatedly passed through the reactor.

7. A method as described in claim 4 wherein the removed t-alkylated xylenols are fractionated to recover 6-t-alkyl-2,4-xylenol, said 6-t-alkyl-2,4-xylenol then dealkylated over a silica-alumina catalyst at temperatures of from about 200° to about 220° C. and about ambient pressure.

8. A method as described in claim 5 wherein the process is carried out continuously with an LHSV from about 0.5 to about 0.8.

* * * * *